United States Patent
Abunassar (10) Patent No.: US 12,121,439 B2
(45) Date of Patent: Oct. 22, 2024

(54) BIASED DISTAL ASSEMBLIES WITH LOCKING MECHANISM

(71) Applicant: EVALVE, INC., Santa Clara, CA (US)

(72) Inventor: Chad Abunassar, San Francisco, CA (US)

(73) Assignee: EVALVE, INC., Santa Clara, CA (US)

(*) Notice: Subject to any disclaimer, the term of this patent is extended or adjusted under 35 U.S.C. 154(b) by 28 days.

(21) Appl. No.: 17/484,203

(22) Filed: Sep. 24, 2021

(65) Prior Publication Data
US 2022/0117737 A1   Apr. 21, 2022

Related U.S. Application Data (60) Provisional application No. 63/092,110, filed on Oct. 15, 2020.

(51) Int. Cl.
*A61F 2/24* (2006.01)
*A61B 17/00* (2006.01)

(52) U.S. Cl.
CPC ...... *A61F 2/2466* (2013.01); *A61B 17/00234* (2013.01); *A61F 2/2454* (2013.01);
(Continued)

(58) Field of Classification Search
CPC .......... A61F 2/2454; A61F 2/246; A61F 2220/0041; A61F 2/2466; A61F 2220/0016; A61F 2220/0091; A61B 2017/00619
See application file for complete search history.

(56) References Cited

U.S. PATENT DOCUMENTS

| 3,378,010 A | 4/1968 | Codling et al. |
| 3,874,388 A | 4/1975 | King et al. |
| (Continued) | | |

FOREIGN PATENT DOCUMENTS

| CA | 2 296 317 C | 1/2009 |
| EP | 0 558 031 B1 | 9/1993 |
| (Continued) | | |

OTHER PUBLICATIONS

International Search report and Written Opinion mailed Jan. 5, 2022 in International Application No. PCT/US2021/051923.

*Primary Examiner* — Melanie R Tyson
*Assistant Examiner* — Cassidy N Stuhlsatz
(74) *Attorney, Agent, or Firm* — SLEMAN & LUND LLP (57) ABSTRACT

System for fixation of native leaflets of a heart valve including an implantable fixation device including a center portion defining a longitudinal axis. The implantable fixation device further includes a first distal assembly having a first distal strut pivotally-coupled with the center portion and a first distal element pivotally-coupled with the first distal strut. The first distal assembly is configured to move between a closed position and an extended position. The implantable fixation device further includes a second distal assembly having a second distal strut pivotally-coupled with the center portion and a second distal element pivotally-coupled with the second distal strut. The second distal assembly is configured to move between a closed position and an extended position. The implantable fixation device further includes a locking mechanism configured to lock the first distal assembly and second distal assembly in a selected locked position between the closed position and the extended position.

20 Claims, 7 Drawing Sheets

(52) U.S. Cl.
CPC .... *A61F 2/246* (2013.01); *A61B 2017/00243* (2013.01); *A61F 2210/0014* (2013.01); *A61F 2220/0016* (2013.01); *A61F 2220/0041* (2013.01); *A61F 2220/0091* (2013.01)

(56) References Cited

U.S. PATENT DOCUMENTS

| | | | |
|---|---|---|---|
| 4,007,743 A | 2/1977 | Blake | |
| 4,055,861 A | 11/1977 | Carpentier et al. | |
| 4,327,736 A | 5/1982 | Inoue | |
| 4,340,091 A | 7/1982 | Skelton et al. | |
| 4,657,024 A | 4/1987 | Coneys | |
| 4,693,248 A | 9/1987 | Failla | |
| 4,716,886 A | 1/1988 | Schulman et al. | |
| 4,795,458 A | 1/1989 | Regan | |
| 4,809,695 A | 3/1989 | Gwathmey et al. | |
| 4,930,674 A | 6/1990 | Barak | |
| 5,002,562 A | 3/1991 | Oberlander | |
| 5,069,679 A | 12/1991 | Taheri | |
| 5,098,440 A | 3/1992 | Hillstead | |
| 5,125,895 A | 6/1992 | Buchbinder et al. | |
| 5,147,370 A | 9/1992 | McNamara et al. | |
| 5,171,259 A | 12/1992 | Inoue | |
| 5,222,963 A | 6/1993 | Brinkerhoff et al. | |
| 5,271,544 A | 12/1993 | Fox et al. | |
| 5,327,905 A | 7/1994 | Avitall | |
| 5,330,501 A | 7/1994 | Tovey et al. | |
| 5,334,217 A | 8/1994 | Das | |
| 5,363,861 A | 11/1994 | Edwards et al. | |
| 5,389,077 A | 2/1995 | Melinyshyn et al. | |
| 5,403,326 A | 4/1995 | Harrison et al. | |
| 5,425,744 A | 6/1995 | Fagan et al. | |
| 5,450,860 A | 9/1995 | O'Connor | |
| 5,452,837 A | 9/1995 | Williamson, IV et al. | |
| 5,456,400 A | 10/1995 | Shichman et al. | |
| 5,456,674 A | 10/1995 | Bos et al. | |
| 5,478,353 A | 12/1995 | Yoon | |
| 5,542,949 A | 8/1996 | Yoon | |
| 5,562,678 A | 10/1996 | Booker | |
| 5,601,224 A | 2/1997 | Bishop et al. | |
| 5,601,574 A | 2/1997 | Stefanchik et al. | |
| 5,607,462 A | 3/1997 | Imran | |
| 5,607,471 A | 3/1997 | Seguin et al. | |
| 5,609,598 A | 3/1997 | Laufer et al. | |
| 5,611,794 A | 3/1997 | Sauer et al. | |
| 5,636,634 A | 6/1997 | Kordis et al. | |
| 5,695,504 A | 12/1997 | Gifford, III et al. | |
| 5,713,911 A | 2/1998 | Racenet et al. | |
| 5,716,417 A | 2/1998 | Girard et al. | |
| 5,741,297 A | 4/1998 | Simon | |
| 5,755,778 A | 5/1998 | Kleshinski | |
| 5,782,239 A | 7/1998 | Webster, Jr. | |
| 5,797,960 A | 8/1998 | Stevens et al. | |
| 5,810,847 A | 9/1998 | Laufer et al. | |
| 5,814,097 A | 9/1998 | Sterman et al. | |
| 5,843,178 A | 12/1998 | Vanney et al. | |
| 5,849,019 A | 12/1998 | Yoon | |
| 5,855,601 A | 1/1999 | Bessler et al. | |
| 5,976,159 A | 11/1999 | Bolduc et al. | |
| 6,015,417 A | 1/2000 | Reynolds, Jr. | |
| 6,048,351 A | 4/2000 | Gordon et al. | |
| 6,079,414 A | 6/2000 | Roth | |
| 6,117,144 A | 9/2000 | Nobles et al. | |
| 6,120,496 A | 9/2000 | Whayne et al. | |
| 6,149,658 A | 11/2000 | Gardiner et al. | |
| 6,165,183 A | 12/2000 | Kuehn et al. | |
| 6,182,664 B1 | 2/2001 | Cosgrove | |
| 6,193,734 B1 | 2/2001 | Bolduc et al. | |
| 6,200,315 B1 | 3/2001 | Gaiser et al. | |
| 6,217,528 B1 | 4/2001 | Koblish et al. | |
| 6,269,819 B1 | 8/2001 | Oz et al. | |
| 6,290,674 B1 | 9/2001 | Roue et al. | |
| 6,312,447 B1 | 11/2001 | Grimes | |
| 6,332,880 B1 | 12/2001 | Yang et al. | |
| 6,346,074 B1 | 2/2002 | Roth | |
| 6,419,696 B1 | 7/2002 | Ortiz et al. | |
| 6,461,366 B1 | 10/2002 | Seguin | |
| 6,482,224 B1 | 11/2002 | Michler et al. | |
| 6,496,420 B2 | 12/2002 | Manning | |
| 6,544,215 B1 | 4/2003 | Bencini et al. | |
| 6,551,303 B1 | 4/2003 | Van Tassel et al. | |
| 6,575,971 B2 | 6/2003 | Hauck et al. | |
| 6,599,311 B1 | 7/2003 | Biggs et al. | |
| 6,626,930 B1 | 9/2003 | Allen et al. | |
| 6,629,534 B1 | 10/2003 | St. Goar et al. | |
| 6,669,687 B1 | 12/2003 | Saadat | |
| 6,695,866 B1 | 2/2004 | Kuehn et al. | |
| 6,719,767 B1 | 4/2004 | Kimblad | |
| 6,752,813 B2 | 6/2004 | Goldfarb et al. | |
| 6,770,083 B2 | 8/2004 | Seguin | |
| 6,797,002 B2 | 9/2004 | Spence et al. | |
| 6,837,867 B2 | 1/2005 | Kortelling | |
| 6,855,137 B2 | 2/2005 | Bon | |
| 6,875,224 B2 | 4/2005 | Grimes | |
| 6,908,481 B2 | 6/2005 | Cribier | |
| 6,926,730 B1 | 8/2005 | Nguyen et al. | |
| 7,011,669 B2 | 3/2006 | Kimblad | |
| 7,101,395 B2 | 9/2006 | Tremulis et al. | |
| 7,112,207 B2 | 9/2006 | Allen et al. | |
| 7,125,421 B2 | 10/2006 | Tremulis et al. | |
| 7,226,467 B2 | 6/2007 | Lucatero et al. | |
| 7,556,632 B2 | 7/2009 | Zadno | |
| 7,563,267 B2 | 7/2009 | Goldfarb et al. | |
| 7,569,062 B1 | 8/2009 | Kuehn et al. | |
| 7,604,646 B2 | 10/2009 | Goldfarb et al. | |
| 7,635,329 B2 | 12/2009 | Goldfarb et al. | |
| 7,655,015 B2 | 2/2010 | Goldfarb et al. | |
| 7,666,204 B2 | 2/2010 | Thornton et al. | |
| 7,736,388 B2 | 6/2010 | Goldfarb et al. | |
| 7,811,296 B2 | 10/2010 | Goldfarb et al. | |
| 7,972,323 B1 | 7/2011 | Bencini et al. | |
| 7,981,139 B2 | 7/2011 | Martin et al. | |
| 8,057,493 B2 | 11/2011 | Goldfarb et al. | |
| 8,062,313 B2 | 11/2011 | Kimblad | |
| 8,118,822 B2 | 2/2012 | Schaller et al. | |
| 8,216,230 B2 | 7/2012 | Hauck et al. | |
| 8,216,256 B2 | 7/2012 | Raschdorf, Jr. et al. | |
| 8,303,608 B2 | 11/2012 | Goldfarb et al. | |
| 8,500,761 B2 | 8/2013 | Goldfarb et al. | |
| 8,734,505 B2 | 5/2014 | Goldfarb et al. | |
| 8,740,920 B2 | 6/2014 | Goldfarb et al. | |
| 9,510,829 B2 | 12/2016 | Goldfarb et al. | |
| 10,076,415 B1 | 9/2018 | Metchik et al. | |
| 10,105,222 B1 | 10/2018 | Metchik et al. | |
| 10,123,873 B1 | 11/2018 | Metchik et al. | |
| 10,130,475 B1 | 11/2018 | Metchik et al. | |
| 10,136,993 B1 | 11/2018 | Metchik et al. | |
| 10,159,570 B1 | 12/2018 | Metchik et al. | |
| 10,231,837 B1 | 3/2019 | Metchik et al. | |
| 10,238,493 B1 | 3/2019 | Metchik et al. | |
| 10,245,144 B1 | 4/2019 | Metchik et al. | |
| D847,983 S | 5/2019 | Ho et al. | |
| 10,314,586 B2 | 6/2019 | Greenberg et al. | |
| 10,413,408 B2 | 9/2019 | Krone et al. | |
| 10,507,109 B2 | 12/2019 | Metchik et al. | |
| 10,517,726 B2 | 12/2019 | Chau et al. | |
| 10,524,792 B2 | 1/2020 | Hernandez et al. | |
| 10,595,997 B2 * | 3/2020 | Metchik | A61F 2/2463 |
| 10,646,342 B1 | 5/2020 | Marr et al. | |
| 10,779,837 B2 | 9/2020 | Lee et al. | |
| D902,403 S | 11/2020 | Marsot et al. | |
| 10,856,988 B2 | 12/2020 | McNiven et al. | |
| 2002/0013571 A1 | 1/2002 | Goldfarb et al. | |
| 2002/0183787 A1 | 12/2002 | Wahr et al. | |
| 2003/0069593 A1 | 4/2003 | Tremulis et al. | |
| 2003/0167071 A1 | 9/2003 | Martin et al. | |
| 2004/0034365 A1 | 2/2004 | Lentz et al. | |
| 2004/0044350 A1 | 3/2004 | Martin et al. | |
| 2005/0267493 A1 | 12/2005 | Schreck et al. | |
| 2006/0020275 A1 * | 1/2006 | Goldfarb | A61B 17/08 606/151 |
| 2007/0038293 A1 | 2/2007 | St. Goar et al. | |
| 2013/0066341 A1 * | 3/2013 | Ketai | A61F 2/246 606/151 |

(56) References Cited

U.S. PATENT DOCUMENTS

| | | |
|---|---|---|
| 2017/0042546 A1 | 2/2017 | Goldfarb et al. |
| 2017/0049455 A1 | 2/2017 | Seguin |
| 2017/0239048 A1 | 8/2017 | Goldfarb et al. |
| 2017/0265994 A1 | 9/2017 | Krone |
| 2018/0021133 A1 | 1/2018 | Barbarino |
| 2018/0036119 A1 | 2/2018 | Wei et al. |
| 2018/0092661 A1 | 4/2018 | Prabhu |
| 2018/0146964 A1 | 5/2018 | Garcia et al. |
| 2018/0235657 A1 | 8/2018 | Abunassar |
| 2018/0242976 A1 | 8/2018 | Kizuka |
| 2018/0243086 A1 | 8/2018 | Barbarino et al. |
| 2018/0325661 A1* | 11/2018 | Delgado ............ A61B 17/1227 |
| 2018/0325671 A1 | 11/2018 | Abunassar et al. |
| 2018/0344460 A1 | 12/2018 | Wei |
| 2018/0353181 A1 | 12/2018 | Wei |
| 2018/0360457 A1 | 12/2018 | Ellis et al. |
| 2019/0000613 A1* | 1/2019 | Delgado ............ A61B 17/3468 |
| 2019/0053803 A1 | 2/2019 | Ketai et al. |
| 2019/0125536 A1 | 5/2019 | Prabhu et al. |
| 2019/0151041 A1 | 5/2019 | Ho et al. |
| 2019/0151089 A1 | 5/2019 | Wei |
| 2019/0159899 A1 | 5/2019 | Marsot et al. |
| 2019/0167197 A1 | 6/2019 | Abunassar et al. |
| 2019/0183571 A1 | 6/2019 | De Marchena |
| 2019/0209293 A1 | 7/2019 | Metchik et al. |
| 2019/0247187 A1 | 8/2019 | Kizuka |
| 2019/0274831 A1 | 9/2019 | Prabhu |
| 2019/0321166 A1* | 10/2019 | Freschauf ............... A61F 2/246 |
| 2019/0321597 A1 | 10/2019 | Van Hoven et al. |
| 2019/0343630 A1 | 11/2019 | Kizuka |
| 2019/0350702 A1 | 11/2019 | Hernandez |
| 2019/0350710 A1 | 11/2019 | Ketai et al. |
| 2019/0365536 A1 | 12/2019 | Prabhu |
| 2020/0000473 A1* | 1/2020 | Dell ..................... A61B 17/10 |
| 2020/0060687 A1* | 2/2020 | Hernández ............ A61F 2/2466 |
| 2020/0078173 A1 | 3/2020 | McNiven et al. |
| 2020/0113678 A1 | 4/2020 | McCann et al. |
| 2020/0121460 A1 | 4/2020 | Dale et al. |
| 2020/0121894 A1 | 4/2020 | Prabhu et al. |
| 2020/0138567 A1 | 5/2020 | Marr et al. |
| 2020/0187942 A1 | 6/2020 | Wei |
| 2020/0205829 A1* | 7/2020 | Wei ........................ A61F 2/246 |
| 2020/0245998 A1 | 8/2020 | Basude et al. |
| 2020/0261107 A1 | 8/2020 | Cohen |
| 2020/0281591 A1 | 9/2020 | Krone et al. |
| 2020/0315786 A1 | 10/2020 | Metchik et al. |
| 2020/0323528 A1 | 10/2020 | Khairkhahan |
| 2020/0323549 A1 | 10/2020 | Goldfarb et al. |
| 2020/0323634 A1 | 10/2020 | Von Oepen et al. |
| 2020/0360018 A1 | 11/2020 | Dell et al. |
| 2020/0367871 A1 | 11/2020 | Van Hoven et al. |

FOREIGN PATENT DOCUMENTS

| | | |
|---|---|---|
| EP | 1 383 448 B1 | 6/2008 |
| FR | 2 768 324 A1 | 3/1999 |
| FR | 2 768 325 B1 | 11/1999 |
| WO | WO 91/01689 A1 | 2/1991 |
| WO | WO 92/12690 A1 | 8/1992 |
| WO | WO 94/018893 A1 | 9/1994 |
| WO | WO 96/32882 A1 | 10/1996 |
| WO | WO 97/27807 A1 | 8/1997 |
| WO | WO 98/07375 A1 | 2/1998 |
| WO | WO 99/07354 A2 | 2/1999 |
| WO | WO 99/13777 A1 | 3/1999 |
| WO | WO 99/15223 A1 | 4/1999 |
| WO | WO 00/03759 A2 | 1/2000 |
| WO | WO 00/60995 A2 | 10/2000 |
| WO | WO 01/28432 A1 | 4/2001 |
| WO | WO 03/020179 A1 | 3/2003 |
| WO | WO 03/049619 A2 | 6/2003 |
| WO | WO 2015/057289 A1 | 4/2015 |
| WO | WO 2016/178722 A1 | 11/2016 |
| WO | WO 2018/093663 A1 | 5/2018 |
| WO | WO 2020/176410 A1 | 9/2020 |

* cited by examiner

BIASED DISTAL ASSEMBLIES WITH LOCKING MECHANISM

CROSS-REFERENCE TO RELATED APPLICATIONS

This application claims the benefit, under 35 U.S.C. § 119(e), of U.S. Provisional Patent Application No. 63/092,110, filed Oct. 15, 2020, which is incorporated herein by reference.

FIELD OF DISCLOSED SUBJECT MATTER

The disclosed subject matter is directed to medical devices for the endovascular, percutaneous or minimally invasive surgical treatment of bodily tissues, such as tissue approximation or valve repair. More particularly, the present disclosure relates to repair of valves of the heart and venous valves.

Surgical repair of bodily tissues can involve tissue approximation and fastening of such tissues in the approximated arrangement. When repairing valves, tissue approximation includes coapting the leaflets of the valves in a therapeutic arrangement which can then be maintained by fastening or fixing the leaflets. Such coaptation can be used to treat regurgitation, which commonly occurs in the mitral valve and in the tricuspid valve.

Mitral valve regurgitation is characterized by retrograde flow from the left ventricle of a heart through an incompetent mitral valve into the left atrium. During a normal cycle of heart contraction (systole), the mitral valve acts as a check valve to prevent flow of oxygenated blood back into the left atrium. In this way, the oxygenated blood is pumped into the aorta through the aortic valve. Regurgitation of the mitral valve can significantly decrease the pumping efficiency of the heart, placing the patient at risk of severe, progressive heart failure.

Mitral valve regurgitation can result from a number of different mechanical defects in the mitral valve or the left ventricular wall. The valve leaflets, the valve chordae which connect the leaflets to the papillary muscles, the papillary muscles or the left ventricular wall can be damaged or otherwise dysfunctional. Commonly, the valve annulus can be damaged, dilated, or weakened limiting the ability of the mitral valve to close adequately against the high pressures of the left ventricle.

DESCRIPTION OF RELATED ART

Treatments for mitral valve regurgitation rely on valve replacement or repair including leaflet and annulus remodeling, the latter generally referred to as valve annuloplasty. Another technique for mitral valve repair, which relies on suturing adjacent segments of the opposed valve leaflets together is referred to as the "bow-tie" or "edge-to-edge" technique. Preferably, the use of devices and systems should not require open chest access and, rather, be capable of being performed either endovascularly, i.e., using devices, such as a catheter, which are advanced to the heart from a point in the patient's vasculature remote from the heart. Furthermore, such devices and systems should allow for repositioning and optional removal of a fixation device (i.e., valve repair clip) prior to fixation to ensure optimal placement. Such devices and systems likewise can be useful for repair of tissues in the body other than heart valves.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter is directed to a fixation device for treating a patient.

In accordance with the disclosed subject matter, a system for fixation of native leaflets of a heart valve including an implantable fixation device including a center portion defining a longitudinal axis. The implantable fixation device further includes a first distal assembly having a first distal strut pivotally-coupled with the center portion and a first distal element pivotally-coupled with the first distal strut. The first distal assembly is configured to move between a closed position with the first distal strut folded proximate the center portion and the first distal element folded proximate the first distal strut, and an extended position with the first distal strut extending distally from the center portion and the first distal element extends distally from the first distal strut. The first distal assembly is biased towards the closed position. The implantable fixation device further includes a second distal assembly having a second distal strut pivotally-coupled with the center portion and a second distal element pivotally-coupled with the second distal strut. The second distal assembly is configured to move between a closed position with the second distal strut folded proximate the center portion and the second distal element folded proximate the second distal strut, and an extended position with the second distal strut extending distally from the center portion and the second distal element extending distally from the second distal strut. The second distal assembly is biased towards the closed position.

The implantable fixation device further includes a first proximal element having a first gripping portion. The first gripping portion is moveable relative to the first distal assembly to capture native leaflet tissue therebetween. The implantable fixation device further includes a second proximal element having a second gripping portion. The second gripping portion is moveable relative to the second distal assembly to capture native leaflet tissue therebetween. The implantable fixation device further includes a locking mechanism configured to lock the first distal assembly and second distal assembly in a selected locked position between the closed position and the extended position.

In accordance with the disclosed subject matter, the center portion can include a smooth surface. The center portion can be configured to obstruct regurgitant blood flow between native leaflets of the heart valve. Each of the first and second distal assemblies can comprise a plurality of stamped metal components having at least one rivet attachment. Each of the first and second distal assemblies can be made of a single-piece, braided structure. The first and second distal assemblies can be biased towards the closed position by at least one spring. The at least one spring can produce between about 0.10 lbf and 0.50 lbf of closure force at each of the first and second distal struts measured proximate a location of coupling between the first and second distal struts and the first and second distal elements, respectively. The implantable fixation device can further include an actuator shaft operatively connected to the first and second distal assemblies, and the at least one spring is an axial spring operatively connected to the actuator shaft. Additionally or alternatively, the at least one spring can be a torsion spring operatively connected to at least one pivot point of each of the first and second distal assemblies. Additionally or alternatively, each of the first and second distal assemblies can include a flexural member configured to bias each of the first and second distal assemblies towards the closed position, wherein the flexural member can be made of nitinol and can include a beam structure selected from the group consisting of a slotted beam, a solid beam, and a hinged beam. Further, each of the flexural members can comprise a living hinge at a pivot point of the first and second distal assemblies, respectively, with the strain-free condition set in the fully closed condition.

Further, each of the first and second proximal elements can be attached to the center portion. Alternatively, the first proximal element can be attached to the first distal strut and the second proximal element can be attached to the second distal strut.

In accordance with another aspect of the disclosed subject matter, the locking mechanism can include a binding plate configured to lock each of the first and second distal assemblies when the binding plate is at an angled orientation relative to the longitudinal axis and further configured to unlock each of the first and second distal assemblies when the binding plate is at a perpendicular orientation relative to the longitudinal axis.

Additionally, the system for fixation can further include a delivery device releasably attached to the implantable fixation device, the delivery device can include an actuator rod, wherein the implantable fixation device can be releasably attached to the implantable fixation device at a distal end of the actuator rod. The actuator rod can be rotatable and can include a threaded fastener at the distal end thereof. The threaded fastener can be configured to connect to the implantable fixation device by a threaded connection. Distal movement of the actuator rod moves each of the first and second distal assemblies towards the extended position, and proximal movement of the actuator rod moves each of the first and second distal assemblies towards the closed position.

DETAILED DESCRIPTION

Reference will now be made in detail to the various exemplary embodiments of the disclosed subject matter, exemplary embodiments of which are illustrated in the accompanying drawings.

The fixation device for use with the disclosed subject matter provides an edge-to-edge transcatheter valve repair option for patients having various conditions, including regurgitant mitral valves or tricuspid valves. Transcatheter (e.g., trans-septal) edge-to-edge valve repair has been established using a fixation device. These fixation devices generally are configured to capture and secure opposing native leaflets using two types of leaflet contacting elements. The first element is a sub-valvular element to contact the ventricular side of a native leaflet to be grasped. With the sub-valvular element positioned underneath to stabilize the native leaflet in a beating heart, a second elastic proximal element can be lowered or moved toward the sub-valvular element and into contact with the atrial side of the native leaflet to capture the leaflet therebetween. Once each native leaflet is captured by a respective sub-valvular and proximal element, the fixation device can be closed by raising or moving the sub-valvular element toward a center of the fixation device such that the leaflets are brought into coaptation, which results in a reduction in valvular regurgitation during ventricular systole. Furthermore, a covering can be provided on the sub-valvular and/or proximal element to facilitate tissue ingrowth with the captured leaflets.

Additional details of exemplary fixation devices in accordance with the disclosed subject matter are set forth below. Furthermore, a number of patents and publications disclose additional details and aspects of related fixation devices and operations. See for example, U.S. Pat. No. 7,226,467 to Lucatero et al.; U.S. Pat. No. 7,563,267 to Goldfarb et al.; U.S. Pat. No. 7,655,015 to Goldfarb et al.; U.S. Pat. No. 7,736,388 to Goldfarb et al.; U.S. Pat. No. 7,811,296 to Goldfarb et al.; U.S. Pat. No. 8,057,493 to Goldfarb et al.; U.S. Pat. No. 8,303,608 to Goldfarb et al.; U.S. Pat. No. 8,500,761 to Goldfarb et al.; U.S. Pat. No. 8,734,505 to Goldfarb et al.; U.S. Pat. No. 8,740,920 to Goldfarb et al.; U.S. Pat. No. 9,510,829 to Goldfarb et al.; U.S. Pat. No. 7,635,329 to Goldfarb et al.; U.S. Patent Application Publication No. 2017/0042546 to Goldfarb et al.; U.S. Patent Application Publication No. 2017/0239048 to Goldfarb et al.; U.S. Patent Application Publication No. 2018/0325671 to Abunassar et al., the entirety of the contents of each of these patents and published applications is incorporated herein by reference.

In fixing leaflets of a heart valve, an implantable fixation device with sub-valvular elements can be self-closing (i.e., biased towards a closed position), which can have advantages for simplifying an implantation procedure. Self-closing sub-valvular elements can be in a final closing angle when a total leaflet resistance force and an internal self-closing force of the sub-valvular elements are equal, thus creating a final equilibrium closing angle. In various circumstances, there are advantages to manually adjusting and fine tuning the final closing angle, thereby modifying the angle to be more open or closed as compared to final equilibrium closing angle. This can allow a user to improve performance of the implantable fixation device in certain situations (e.g., in patients having certain abnormal valve anatomies). When the closing angle is modified, this allows for a direct impact on the tradeoff between regurgitation reduction and diastolic pressure gradient, which is associated with valve stenosis.

In some situations, it can be beneficial to selectively open the angle from the equilibrium closing angle. For example, for relatively small valves, opening the angle can reduce leaflet coaptation to allow more forward blood flow, and thus reduce the possibility of a high gradient. Likewise, when leaflets are particularly vulnerable (e.g., thin, friable, short, or calcified) opening the angle can reduce forces on the leaflets and consequently reduce the probability of a leaflet tear. Alternatively, in other situations and circumstances, it can conversely be beneficial to selectively close the angle beyond the equilibrium closing angle. For example, for valves having abnormally large gaps between leaflets, further closing the angle can reduce excessive regurgitation and improve grasping performance, thus reducing the probability of requiring additional implanted devices to sufficiently reduce regurgitation. Likewise, for valves having uneven leaflets, further closing the angle can ensure the thinner of the two leaflets is sufficiently grasped. Indeed, in a purely self-closing device grasping uneven leaflets, the device will only close to the point of first resistance, such as when the thicker of two inserted leaflets is contacted, which can leave the thinner leaflet insufficiently grasped.

Accordingly, a self-closing (biased closed) device can be combined with one or more additional features, such as a locking mechanism, to enable manual selection and fine-tuning of the final closed angle.

Generally, and as set forth in greater detail below, the disclosed subject matter provided herein includes a system for fixation of native leaflets of a heart valve including an implantable fixation device including a center portion defining a longitudinal axis. The implantable fixation device further includes a first distal assembly having a first distal strut pivotally-coupled with the center portion and a first distal element pivotally-coupled with the first distal strut. The first distal assembly is configured to move between a closed position with the first distal strut folded proximate the center portion and the first distal element folded proximate the first distal strut, and an extended position with the first distal strut extending distally from the center portion and the first distal element extends distally from the first distal strut. The first distal assembly is biased towards the closed position. The implantable fixation device further includes a second distal assembly having a second distal strut pivotally-coupled with the center portion and a second distal element pivotally-coupled with the second distal strut. The second distal assembly is configured to move between a closed position with the second distal strut folded proximate the center portion and the second distal element folded proximate the second distal strut, and an extended position with the second distal strut extending distally from the center portion and the second distal element extending distally from the second distal strut. The second distal assembly is biased towards the closed position.

The implantable fixation device further includes a first proximal element having a first gripping portion. The first gripping portion is moveable relative to the first distal assembly to capture native leaflet tissue therebetween. Likewise, the implantable fixation device further includes a second proximal element having a second gripping portion. Similarly, the second gripping portion is moveable relative to the second distal assembly to capture native leaflet tissue therebetween. Additionally, the implantable fixation device further includes a locking mechanism configured to lock the first distal assembly and second distal assembly in a selected locked position between the closed position and the extended position.

Referring to FIGS. 1 and 2A-2C, for the purpose of illustration and not limitation, a system for fixation of native leaflets of a heart valve includes an implantable fixation device 102 comprising a center portion 104 defining a longitudinal axis 106. Additionally, the center portion 104 can include a smooth surface. The smooth surface finish can the provide favorable blood flow obstruction characteristics.

Figure 1:
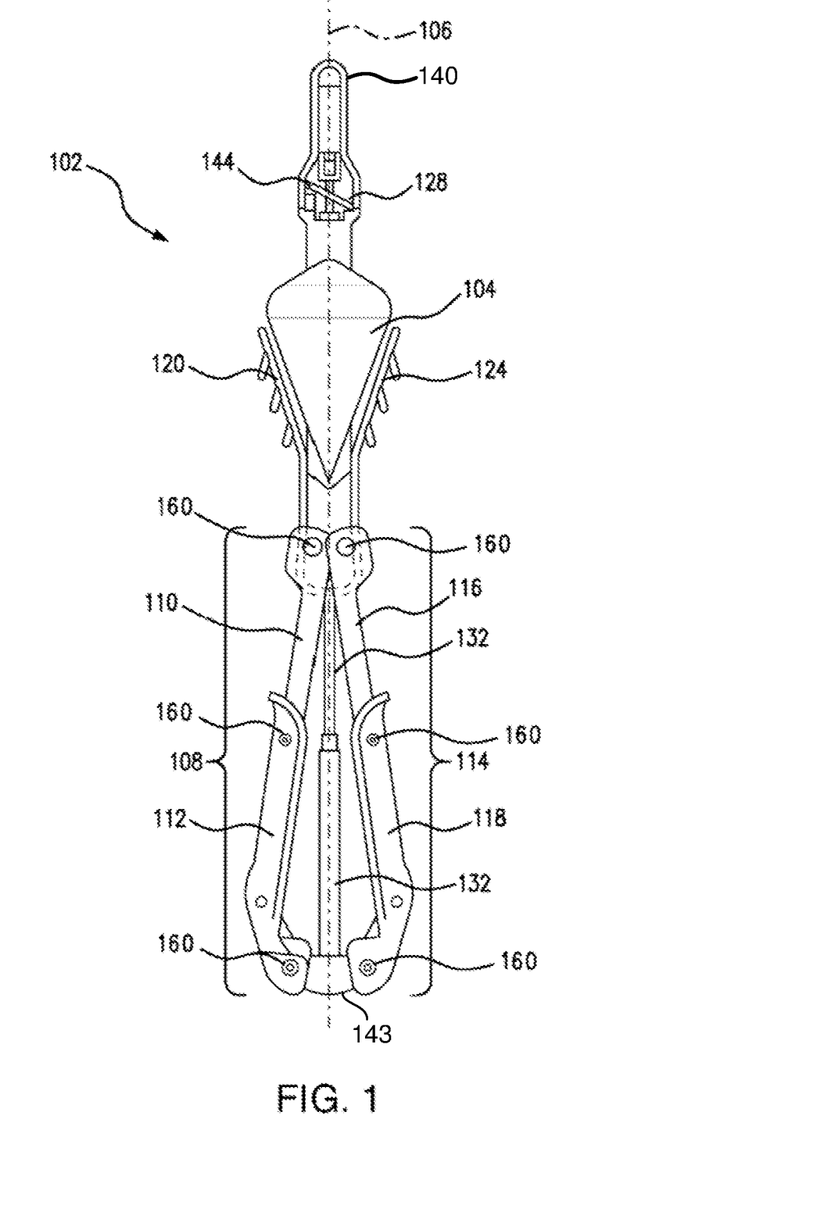
FIG. 1 is a front view of an exemplary embodiment of an implantable fixation device for use in accordance with the disclosed subject matter, the implantable fixation device having distal assemblies in the extended position.

The center portion 104 can be configured to obstruct regurgitant blood flow between native leaflets of the heart valve. Furthermore, the center portion 104 can be configured as a spacer in the valve providing a leaflet sealing surface.

In accordance with the disclosed subject matter, the implantable fixation device 102 further includes a first distal assembly 108 comprising a first distal strut 110 pivotally-coupled with the center portion 104 and a first distal element 112 pivotally-coupled with the first distal strut 110. The first distal assembly 108 is configured to move between a closed position with the first distal strut 110 folded proximate the center portion 104 and the first distal element 112 folded proximate the first distal strut 110, and an extended position with the first distal strut 110 extending distally from the center portion 104 and the first distal element 112 extending distally from the first distal strut 110. The first distal assembly 108 is biased towards the closed position. The implantable fixation device 102 further includes a second distal assembly 114 comprising a second distal strut 116 pivotally-coupled with the center portion 104 and a second distal element 118 pivotally-coupled with the second distal strut 116. The second distal assembly 114 is configured to move between a closed position with the second distal strut 116 folded proximate the center portion 104 and the second distal element 118 folded proximate the second distal strut 116, and an extended position with the second distal strut 116 extending distally from the center portion 104 and the second distal element 118 extending distally from the second distal strut 116. Furthermore, the second distal assembly 114 is biased towards the closed position.

As embodied herein, each of the first and second distal assemblies 108, 114 can comprise a plurality of stamped metal components having at least one rivet attachment 160 attached to a base 143. For example, the distal elements 112, 118 and distal struts 110, 116 may be stamped metal components with various rivet attachment 160 connections connected to base 143, as shown for purpose of illustration and not limitation in FIG. 1. Additionally or alternatively, each of the first and second distal assemblies 108, 114 can be made of a single-piece, braided structure. As another example, each of the first and second distal assemblies can be made of laser-cut metallic sheet structures or nitinol shape-set structures.

Figures 2A, 2B, 2C:
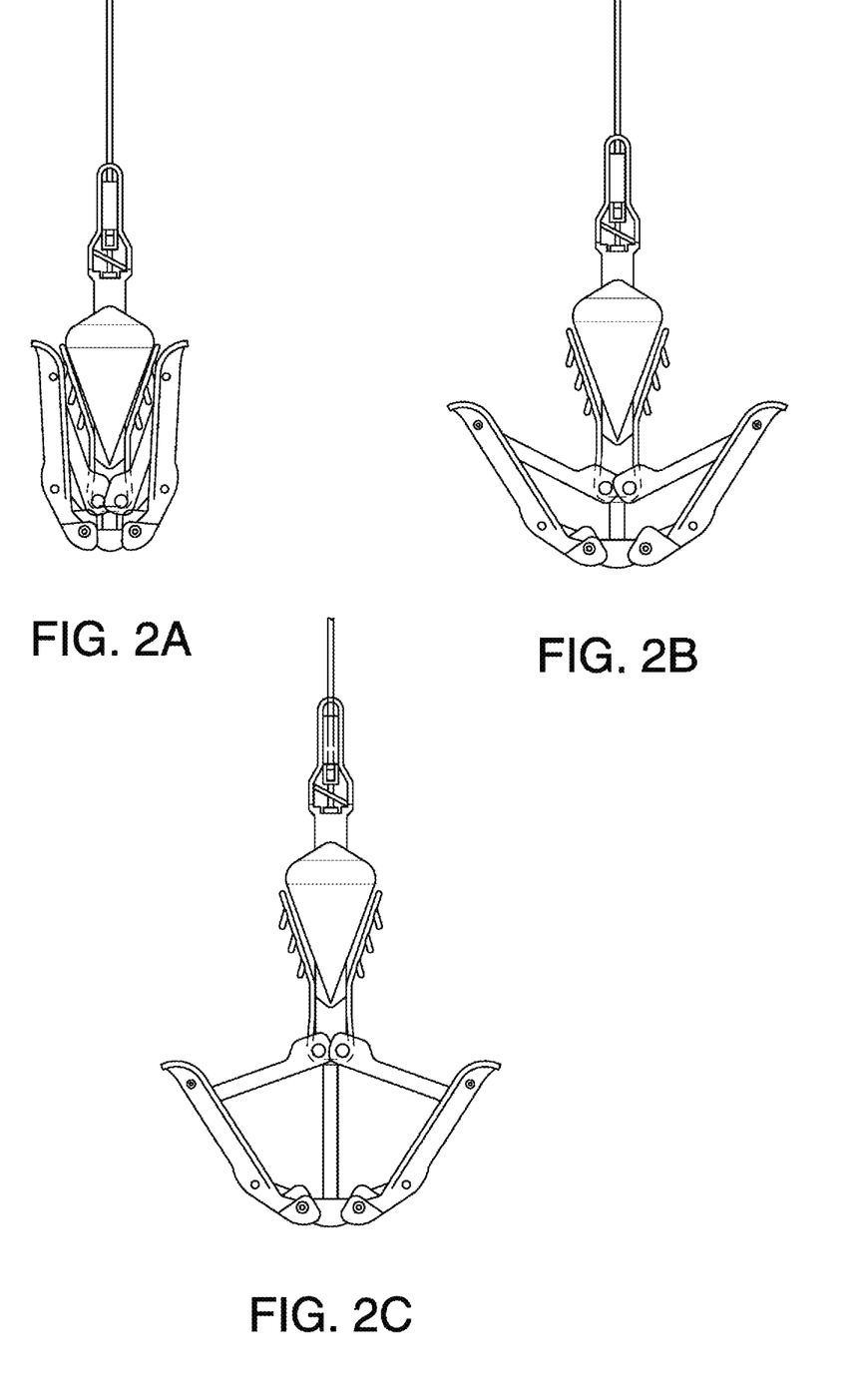
FIGS. 2A-2C are front views of the implantable fixation device of FIG. 1, wherein the distal assemblies are in various non-extended positions.

The extended position can be a fully inverted position of the distal elements 112, 118 configured for delivery of the implantable fixation device 102 and further configured for complete leaflet release. The first and second distal assemblies 108, 114 can be configured to capture a leaflet at various positions between the closed position and the extended position, such as when the angle between the first distal element 112 and the second distal element 118 is between about 110 and 130 degrees, and preferably about 120 degrees. FIG. 2A depicts the first and second distal assemblies 108, 114 in the closed position, and FIGS. 2B and 2C depict the first and second distal assemblies 108, 114 in various positions between the closed and extended positions. The first and second distal assemblies 108, 114 can be sub-valvular elements configured to contact the ventricular side of a native leaflet to be grasped.

In accordance with the disclosed subject matter, and with continued reference to FIG. 1, the implantable fixation device includes a first proximal element 120 having a first gripping portion 122, wherein the first gripping portion 122 is moveable relative to the first distal assembly 108 to capture native leaflet tissue therebetween. Likewise, the implantable fixation device further includes a second proximal element 124 having a second gripping portion 126, wherein the second gripping portion 126 is moveable relative to the second distal assembly 114 to capture native leaflet tissue therebetween. Each of the first and second proximal elements 120, 124 can be attached to the center portion 104. As embodied herein, each proximal element 120, 124 can includes a plurality of friction elements, for example in rows. The friction elements can allow for improved tissue engagement during leaflet capture. In leaflet capture, each first and second proximal element 120, 124 can be lowered or moved toward each respective first and second distal assembly 108,114 and into contact with the atrial side of the native leaflet to capture the leaflet therebetween. The proximal elements 120, 124 and friction elements are described further in the disclosures of the patents and applications incorporated in their entirety by reference herein.

The implantable fixation device, as depicted, further includes a locking mechanism 128 configured to lock the first distal assembly 108 and second distal assembly 114 in a selected locked position between the closed position and the extended position. As shown, and for purpose of illustration and not limitation, the locking mechanism 128 can include a binding plate 144 configured to lock each of the first and second distal assemblies 108, 114 when the binding plate 144 is at an angled orientation relative to the longitudinal axis 106. Further the locking mechanism 128 is configured to unlock each of the first and second distal assemblies 108, 114 when the binding plate 144 is at a perpendicular orientation relative to the longitudinal axis 106. For example, when the binding plate 144 is at the perpendicular orientation, the binding plate 144 can have an internal hole that is clear of an actuator shaft 132 and when the binding plate 144 is in the angled orientation the actuator shaft is engaged and the distal assemblies 108, 114 are locked. Additionally, the locking mechanism 128 can include a release mechanism to remotely control the binding plate 144. The state of the distal assemblies 108, 114 can be actuated between the positions shown in FIGS. 1-2C. Distal movement of the actuator shaft 132 can be arrested by the locking mechanism 128, which therefore provides a one-way lock that prevents the device from opening from more a closed position to a more open position. The actuator shaft 132 may be coupled to base 143, as shown in FIG. 1, such that proximal-distal movement of the actuator shaft 132 correspondingly moves base 142 and moves the first distal assembly 108 and the second distal assembly 114, which may be attached to base 143, between the closed and extended positions. During a procedure, the lock can be remotely configured to an unlocked position by applying tensile force to the binding plate 144. A user may leave the device in an unlocked position for an entire length of a procedure, if desired. Alternatively, the user can only be unlock the device actuating the device to a more open position. As embodied herein, the locking mechanism 128 can comprise a release harness 140, which can adjust the orientation of the binding plate 144 to a perpendicular orientation after a proximal force is applied remotely by from a user (e.g., via a suture connected to the harness). The binding plate 144 can have a locked default angled orientation from a leaf spring component that biases the binding plate. Unlocking the binding plate can unlock the binding plate 144 to a perpendicular orientation relative the longitudinal axis 106 as the leaf spring is compressed elastically. This unlocking force input from is applied by the user through a suture, cable, or line extending through the catheter from a handle to the locking mechanism 128. For simplicity, the lock can be only active on a distal portion of the actuator shaft 132, which can be constructed with a larger diameter than a proximal portion of the actuator shaft 132. Distal portion of the actuator shaft can be made with a rough surface finish such that the lock only functions on the rough surface. A version of the desired locking mechanism 128 is described in U.S. Pat. No. 7,604,646, however, the position of the locking mechanism is modified herein. Further, the locking mechanism 128 in accordance with the disclosed subject matter can include additional and alternative aspects, such as those described in U.S. Pat. No. 7,604,646, the entirety of the contents of which are incorporated herein by reference.

Figure 3A:
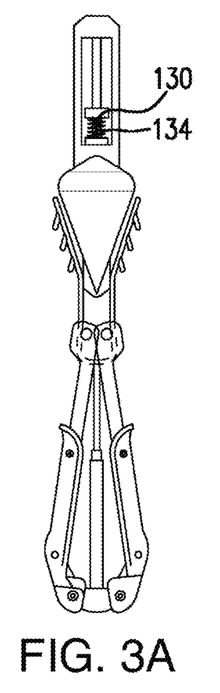
FIGS. 3A-3D are front views of an alternative implantable fixation device including an axial spring.
Figure 3B:
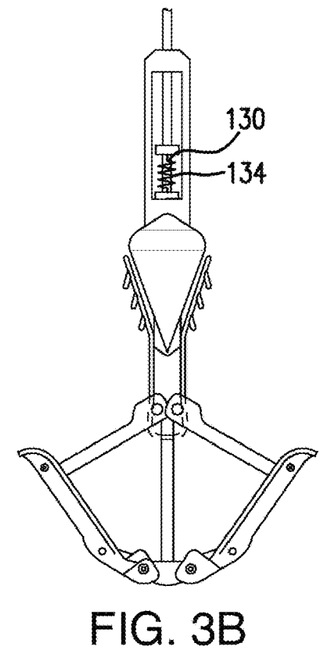
Figure 3C:
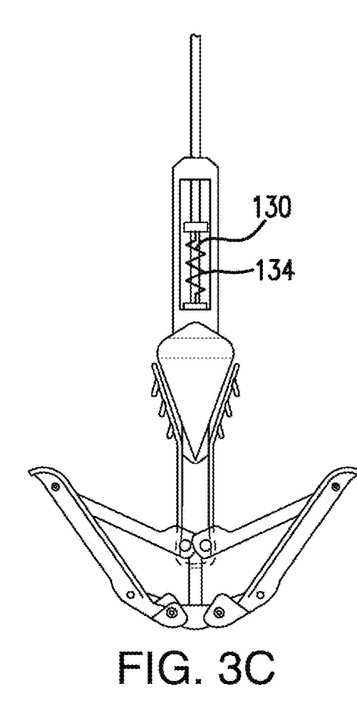
Figure 3D:
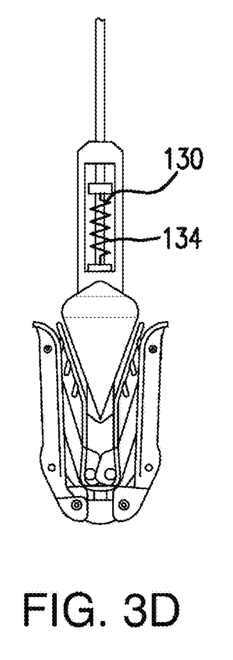

Referring to FIGS. 3A-3D, for illustration and not limitation, the first and second distal assemblies 108, 114 can be biased towards the closed position by at least one spring 130. The at least one spring 130 can produce between about 0.10 lbf and 0.50 lbf of closure force at each of the first and second distal struts 110, 116 at an outer-most location of leaflet contact, which is located proximate a location of coupling between the first and second distal struts 110, 116 and the first and second distal elements 112, 118, respectively. Furthermore, the closure force can resist an anticipated maximum load of about 0.1 to 0.3 lbf with a factor of safety of 2 to 5, or a force range of 0.2 lbf to 1 lbf at a location proximate the location of coupling. FIG. 3D depicts the first and second distal assemblies 108, 114 in the closed position wherein the at least one spring 130 is at a lowest-strain energy state. FIGS. 3B and 3C depict the first and second distal assemblies 108, 114 in various positions between the closed and extended positions, likewise with the at least one spring in various corresponding strain energy states. Additionally, the implantable fixation device can further include an actuator shaft 132 operatively connected to the first and second distal assemblies 108, 114. Further, and as disclosed herein, the at least one spring 130 can be an axial spring 134 operatively connected to the actuator shaft 132. Alternatively, the at least one spring 130 can be a non-axial linear spring. The at least one spring 130 can alternatively be a constant-force spring or a non-linear spring.

Figure 4A:
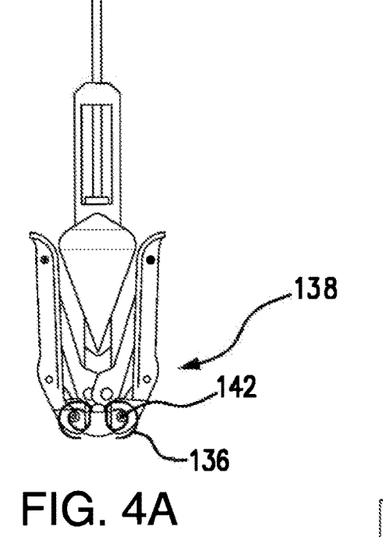
FIGS. 4A-C are front views of an alternative implantable fixation device including a torsion spring.
Figure 4B:
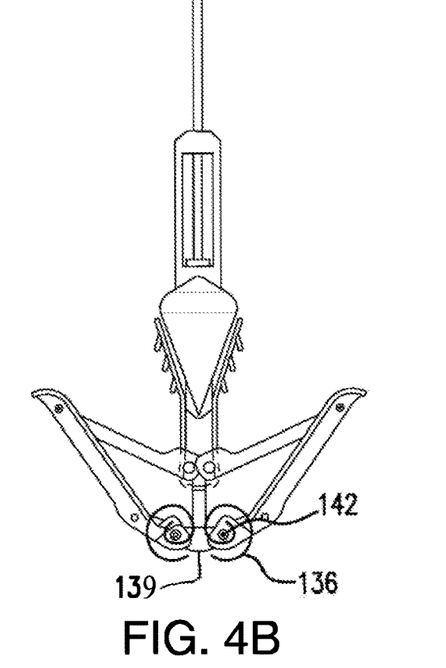
Figure 4C:
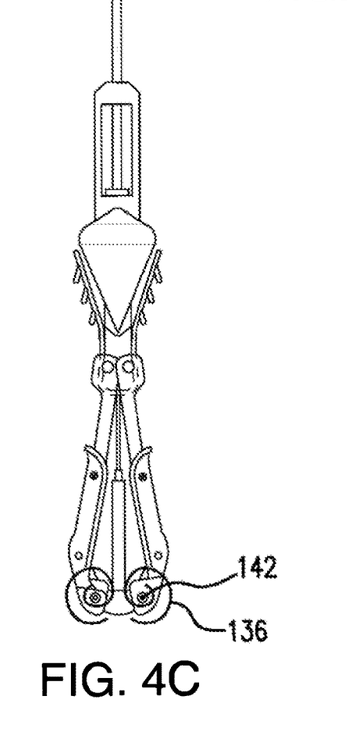

In accordance with the disclosed subject matter, FIGS. 4A-4C illustrate for the purpose of illustration and limitation, that the at least one spring 130 can be a torsion spring 136 operatively connected to at least one pivot point 142 of each of the first and second distal assemblies 108, 114. FIG. 4A depicts the first and second distal assemblies 108, 114 in the closed position wherein the torsion spring 136 is at a lowest-strain energy state. FIGS. 4B and 4C depict the first and second distal assemblies 108, 114 in various positions between the closed and extended positions, likewise with the torsion spring 136 in various corresponding strain energy states.

Additionally or alternatively, each of the first and second distal assemblies 108, 114 can include a flexural member 138 configured to bias each of the first and second distal assemblies 108, 114 towards the closed position. The flexural member 138 can be made of nitinol and can comprise a beam structure 139 selected from the group consisting of a slotted beam, a solid beam, and a hinged beam. Furthermore, each of the flexural members 138 can include a living hinge at a pivot point 142 of the first and second distal assemblies 108, 114, respectively. The flexural members 138 can be integral with any element of the distal assemblies 108, 114. The flexural members can be set to a preferred lowest-strain energy configuration when the distal assemblies 108, 114 are in the closed position by means of shape setting nitinol.

For any biasing mechanism of the disclosed subject matter (e.g., the spring or flexural members), strain energy can be at a lowest-strain energy state when the distal assemblies are fully closed. Further, the biasing mechanism can have an additional lowest-strain energy state when the distal assemblies are fully extended such the that the distal assemblies can also be biased to the extended position. For example, the distal assemblies can be biased to the extended position during delivery, and as the distal assemblies move towards the closed position, the bias can switch to the closed position.

Figure 5A:
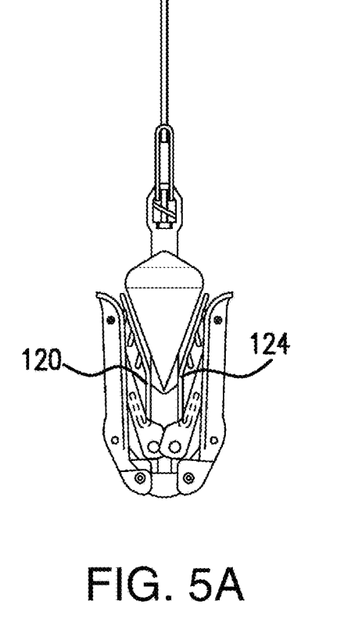
FIGS. 5A-5D are front views of an alternative implantable fixation device having proximal elements attached to distal struts.
Figure 5B:
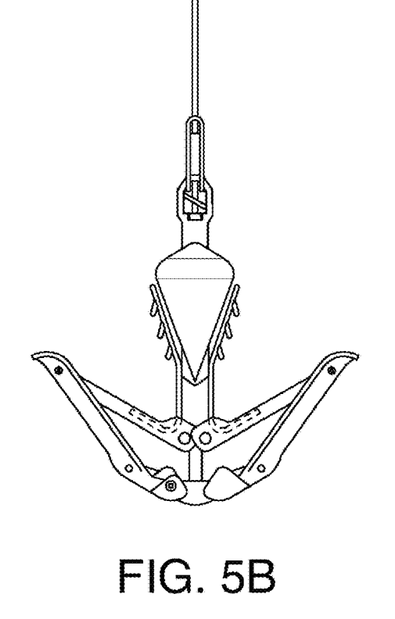
Figure 5C:
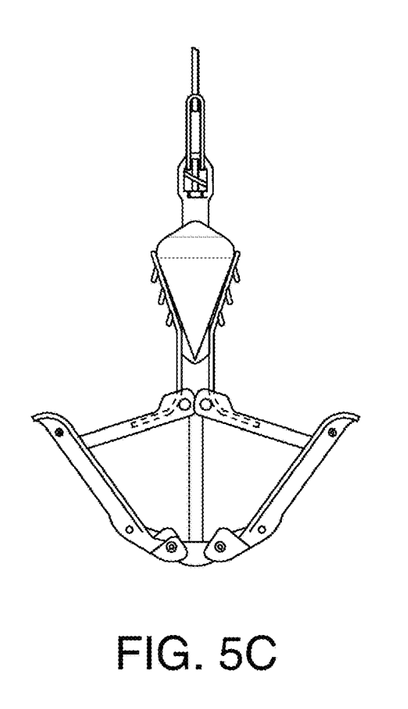
Figure 5D:
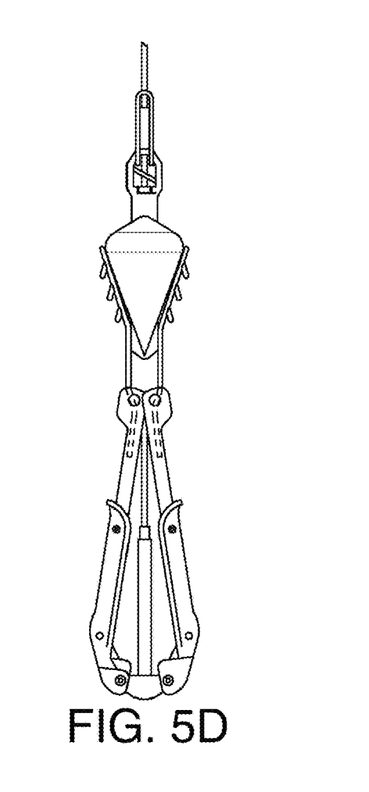

In accordance with another embodiment of the disclosed subject matter, and as shown in FIGS. 5A-D for the purpose of illustration and not limitation, the first proximal element 120 can be attached to the first distal strut 110 and the second proximal element 124 can be attached to the second distal strut 116. Attachment of the proximal element to the distal strut can enable the movement of the distal strut and the proximal element together, which can improve the ability to capture leaflets at relatively open positions of the distal assembly 108, such as the position shown in FIG. 2C. As shown, FIG. 5A depicts the first and second distal assemblies 108, 114 in the closed position, FIG. 5D depicts the first and second assemblies 108, 114 in the extended position and FIGS. 5B-5C depicts the first and second assemblies 108, 114 in various positions between the closed and extended positions.

Figure 6:
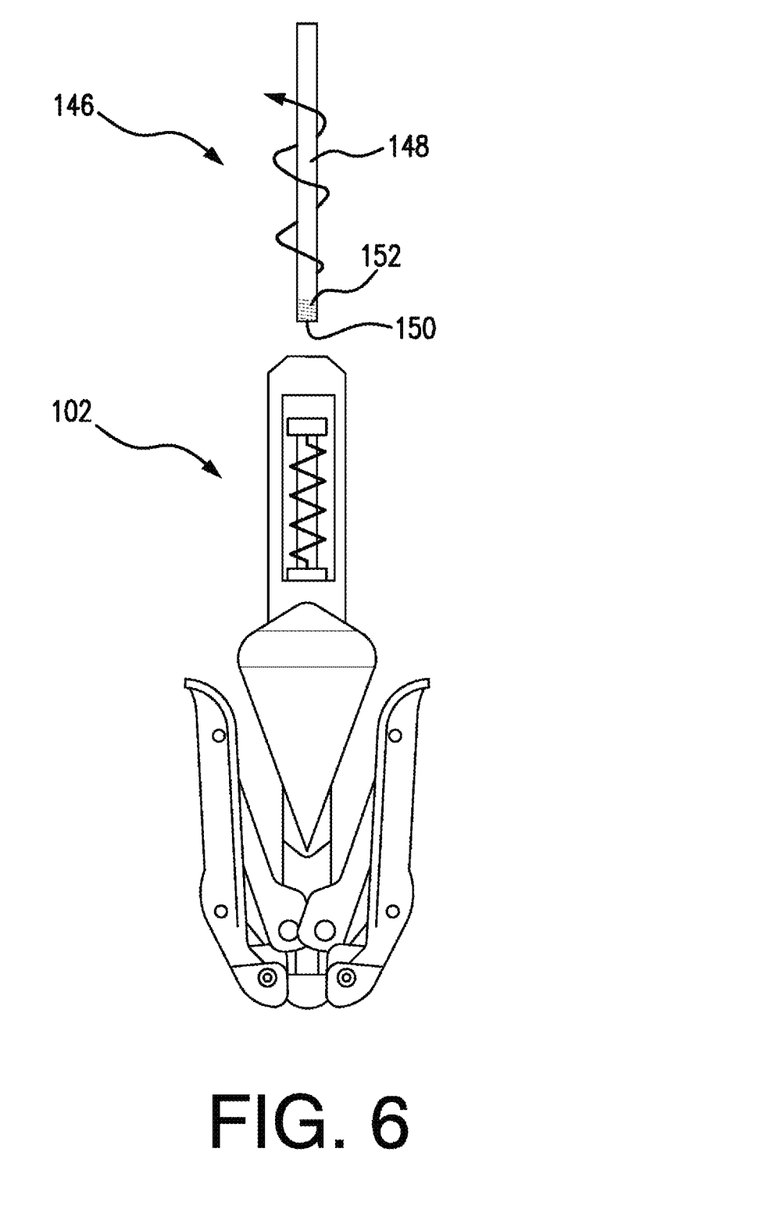
FIG. 6 is a front view of the implantable fixation device of FIGS. 3A-3D and a delivery device configured for releasable attachment.

In accordance with an additional aspect of the subject matter disclosed herein, FIG. 6 depicts, for the purpose of illustration and not limitation, that the system for fixation can include a delivery device 146 releasably attached to the implantable fixation device 102. As shown, the delivery device 146 can include an actuator rod 148, wherein the implantable fixation device 102 can be releasably attached to the implantable fixation device 102 at a distal end 150 of the actuator rod. Furthermore, the actuator rod 148 can be rotatable and comprise a threaded fastener 152 at the distal end 150 thereof. The threaded fastener 152 can be configured to connect to the implantable fixation device 102 by a threaded connection. Furthermore, distal movement of the actuator rod 148 can move each of the first and second distal assemblies 108, 114 towards the extended position, and proximal movement of the actuator rod 148 can move each of the first and second distal assemblies 108, 114 towards the closed position.

Figure 7:
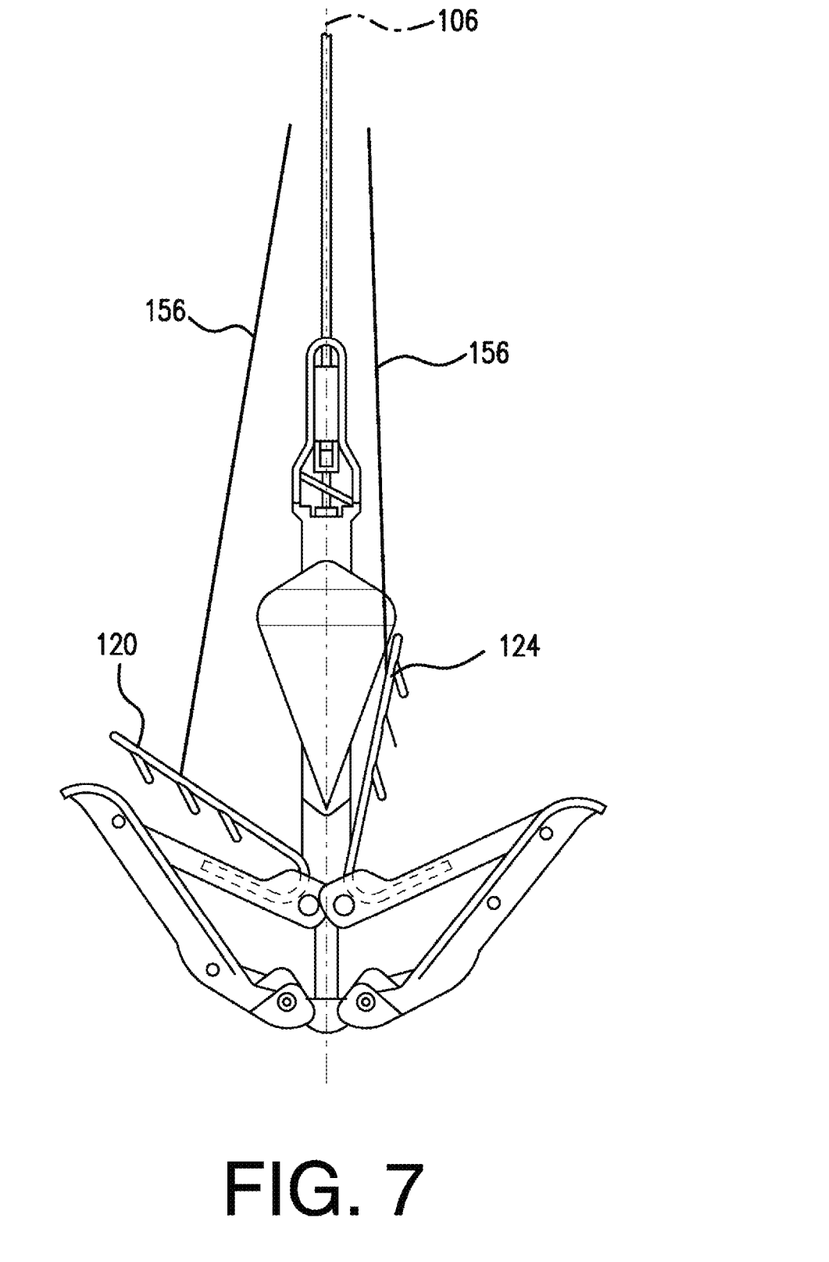
FIG. 7 is a front view of the implantable fixation device of FIGS. 5A-5D further depicting suture lines attached to the proximal elements.

In accordance with a further aspect of the disclosed subject matter, and as further embodied herein in FIG. 7, each of the first and second proximal elements 120, 124 can be biased toward each respective first and second distal assembly 108, 114. Prior to leaflet capture, each proximal element 120, 124 can be moved inwardly toward the longitudinal axis, and, as depicted, held with the aid of one or more proximal element lines 156. The proximal element lines 156 can be in the form of sutures, wires, rods, cables, polymeric lines, or other suitable structures. Furthermore, the one or more proximal element lines 156 can be operatively connected with the first and second proximal elements 120, 124 in a variety of ways, such as by being threaded through loops (not shown) disposed on the first and second proximal elements 120, 124. For purpose of illustration and not limitation, a first proximal element line can be connected to the first proximal element 120 and a second proximal element line can be connected to the second proximal element 124. In leaflet capture, the proximal element lines 156 can lower each first and second proximal element 120, 124 toward each respective first and second distal assembly 108, 114 and into contact with the atrial side of the native leaflet to capture the leaflet therebetween. The proximal element lines 156 are described further in the disclosures of the patents and applications incorporated in their entirety by reference herein.

The embodiments illustrated herein are adapted for repair of a heart valve, such as a mitral valve or a tricuspid valve, using an antegrade approach from a patient's left or right atrium. Prior to a procedure, imaging and various tests can be performed to anticipate and diagnose a patient's individual circumstances and assist a physician in selecting the locked position. For example, when a patient is exhibiting severe backflow, the physician can selectively lock the distal assemblies 108, 114 in the closed position or at an angle of about 10-20 degrees between the first distal element 112 and the second distal element 118. Conversely, when a physician observes significant obstruction to forward flow through the valve being treated, which is termed valve stenosis and characterized by a high pressure gradient across the valve, the physician can elect lock the device at a wider angle of about 30-45 degrees.

While the disclosed subject matter is described herein in terms of certain preferred embodiments for purpose of illustration and not limitation, those skilled in the art will recognize that various modifications and improvements can be made to the disclosed subject matter without departing from the scope thereof. Moreover, although individual features of one embodiment of the disclosed subject matter can be discussed herein or shown in the drawings of one embodiment and not in other embodiments, it should be readily apparent that individual features of one embodiment can be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the system of the disclosed subject matter without departing from the spirit or scope of the disclosed subject matter. Thus, it is intended that the disclosed subject matter include modifications and variations that are within the scope of the appended claims and their equivalents.

The invention claimed is:

1. A system for fixation of native leaflets of a heart valve comprising:
 an implantable fixation device comprising:
  a center portion defining a longitudinal axis;
  a first distal assembly comprising a first distal strut having a first end pivotally-coupled with the center portion and an opposite second end pivotally-coupled with a first distal element, the first distal assembly configured to move between a closed position with the first distal strut folded adjacent the center portion and the first distal element folded adjacent a surface of the first distal strut opposite the center portion, and an extended position with the first distal strut extending distally from the center portion and the first distal element extending distally from the first distal strut, wherein the first distal assembly is spring biased towards the closed position;

a second distal assembly comprising a second distal strut having a first end pivotally-coupled with the center portion and an opposite second end pivotally-coupled with a second distal element, the second distal assembly configured to move between a closed position with the second distal strut folded adjacent the center portion and the second distal element folded adjacent a surface of the second distal strut opposite the center portion, and an extended position with the second distal strut extending distally form the center portion and the second distal element extending distally from the second distal strut, wherein the second distal assembly is spring biased towards the closed position;

an actuator shaft coupled to the first and second distal assemblies and being configured to move the first and second distal assemblies between their respective closed and extended positions upon proximal-distal movement of the actuator shaft;

a first proximal element having a first gripping portion, the first gripping portion being moveable relative to the first distal assembly to capture native leaflet tissue therebetween;

a second proximal element having a second gripping portion, the second gripping portion being moveable relative to the second distal assembly to capture native leaflet tissue therebetween; and a locking mechanism configured to lock the first distal assembly and second distal assembly in a selected locked position between the closed position and the extended position; and a delivery device releasably attached to the implantable fixation device, the delivery device comprising an actuator rod extending therefrom and being releasably engaged to the actuator shaft, the actuator rod being configured to move the actuator shaft in the proximal-distal direction, wherein the locking mechanism is disposed along the longitudinal axis proximal to the center portion and comprises a binding plate and a release harness, the actuator shaft extending through the binding plate and the release harness, the binding plate being disposed within the release harness, and the release harness being configured to adjust an orientation of the binding plate between an angled orientation relative to the actuator shaft to lock each of the first and second distal assemblies and a perpendicular orientation relative to the actuator rod shaft to unlock each of the first and second distal assemblies.

2. The system of claim 1, wherein the center portion comprises a smooth surface.

3. The system of claim 1, wherein the center portion is configured to obstruct regurgitant blood flow between native leaflets of the heart valve.

4. The system of claim 1, wherein each of the first and second distal assemblies comprises a plurality of stamped metal components pivotally-coupled by at least one rivet attachment.

5. The system of claim 1, wherein each of the first and second distal assemblies is made of a single-piece, braided structure.

6. The system of claim 1, wherein the first and second distal assemblies are spring biased towards the closed position by at least one spring.

7. The system of claim 6, wherein the at least one spring produces between about 0.10 lbf and 0.50 lbf of closure force at each of the first and second distal struts, measured proximate a location of coupling between the first and second distal struts and the first and second distal elements.

8. The system of claim 6, wherein the at least one spring is an axial spring and is operatively connected to the actuator shaft.

9. The system of claim 6, wherein the at least one spring is a torsion spring operatively connected to at least one pivot point of each of the first and second distal assemblies.

10. The system of claim 1, wherein each of the first and second distal assemblies comprises a flexural member configured to spring bias each of the first and second distal assemblies towards the closed position, wherein the flexural member is made of nitinol and comprises a beam structure selected from the group consisting of a slotted beam, a solid beam, and a hinged beam.

11. The system of claim 10, wherein each of the flexural members comprises a living hinge at a pivot point of the first and second distal assemblies, respectively.

12. The system of claim 1, wherein each of the first and second proximal elements is attached to the center portion.

13. The system of claim 1, wherein the first proximal element is attached to the first distal strut and the second proximal element is attached to the second distal strut.

14. The system of claim 1, wherein the actuator rod is rotatable and comprises a threaded fastener at the distal end thereof, the threaded fastener configured to connect the actuator shaft of the implantable fixation device by a threaded connection.

15. The system of claim 1, wherein distal movement of the actuator rod moves each of the first and second distal assemblies towards the extended position, and proximal movement of the actuator rod moves each of the first and second distal assemblies towards the closed position.

16. The system of claim 1, wherein the delivery device further comprises a suture extending therefrom, the suture being connected to the release harness such that applying a proximal force to the release harness via the suture adjusts the binding plate to the perpendicular orientation.

17. The system of claim 1, wherein
the implantable fixation device further includes a base coupled to the first and second distal assemblies,
the actuator shaft is coupled to the base such that proximal-distal movement of the actuator shaft correspondingly moves the base in a proximal-distal direction, and
the center portion is positioned between the base and the locking mechanism.

18. The system of claim 1, wherein the actuator shaft extends proximally from the center portion.

19. The system of claim 18, wherein the actuator shaft extends proximally from the center portion after the actuator rod is released therefrom.

20. The system of claim 18, wherein the center portion has a tapered profile such that a proximal end thereof has a larger cross-sectional dimension than a distal end of the center portion.

* * * * *